(12) United States Patent
Guttadauro

(10) Patent No.: US 10,058,410 B2
(45) Date of Patent: Aug. 28, 2018

(54) PROSTHESIS FOR INGUINAL HERNIOPLASTY

(71) Applicant: Angelo Guttadauro, Milan (IT)

(72) Inventor: Angelo Guttadauro, Milan (IT)

( * ) Notice: Subject to any disclaimer, the term of this patent is extended or adjusted under 35 U.S.C. 154(b) by 288 days.

(21) Appl. No.: 14/775,632

(22) PCT Filed: Mar. 12, 2014

(86) PCT No.: PCT/IB2014/059668
§ 371 (c)(1),
(2) Date: Sep. 11, 2015

(87) PCT Pub. No.: WO2014/141087
PCT Pub. Date: Sep. 18, 2014

(65) Prior Publication Data
US 2016/0015503 A1    Jan. 21, 2016

(30) Foreign Application Priority Data

Mar. 14, 2013 (IT) .............................. MI20130090 U
Apr. 19, 2013 (IT) .............................. MI2013A0640

(51) Int. Cl.
*A61F 2/00*          (2006.01)

(52) U.S. Cl.
CPC .... *A61F 2/0063* (2013.01); *A61F 2002/0068* (2013.01)

(58) Field of Classification Search
CPC ............ A61F 2/0063; A61F 2002/0068; A61F 2002/0072
See application file for complete search history.

(56) References Cited

U.S. PATENT DOCUMENTS

| | | | | |
|---|---|---|---|---|
| 8,690,961 | B2 * | 4/2014 | Checa Ayet | .......... A61F 2/0063 623/23.72 |
| 2002/0013590 | A1 * | 1/2002 | Therin | .................. A61F 2/0063 606/151 |
| 2003/0083543 | A1 * | 5/2003 | Nicolo | .................. A61F 2/0063 600/37 |
| 2003/0171823 | A1 * | 9/2003 | Zotti | ..................... A61F 2/0063 623/23.72 |

(Continued)

FOREIGN PATENT DOCUMENTS

| | | |
|---|---|---|
| WO | WO 00/57812 A1 | 10/2000 |
| WO | WO 01/85058 A2 | 11/2001 |
| WO | WO 2011/058340 A1 | 5/2011 |

*Primary Examiner* — David C Eastwood
(74) *Attorney, Agent, or Firm* — DLA Piper LLP (US)

(57) ABSTRACT

The present invention relates to a prosthesis for inguinal hernioplasty made up of a surgical mesh extending from a first end (6) to a second end (7) along a longitudinal direction (A) and comprising a first portion (1) that includes said first end (6), a second portion (2) that includes said second end (7) and a connecting portion (3) arranged between said first portion (1) and said second portion (2), wherein said first portion (1) has a substantially ring shape that is or open or may be opened and is provided with a central hole (4), wherein said second portion (2) has a substantially elongated shape in said longitudinal direction (A), and wherein said connecting portion (3) has a width transverse to said longitudinal direction (A) smaller than the widths of said first portion (1) and said second portion (2) transverse to said longitudinal direction (A).

14 Claims, 4 Drawing Sheets

(56) References Cited

U.S. PATENT DOCUMENTS

| | | | |
|---|---|---|---|
| 2003/0212460 A1* | 11/2003 | Darois | A61F 2/0063 623/23.64 |
| 2005/0165425 A1* | 7/2005 | Croce | A61F 2/0063 606/151 |
| 2005/0192600 A1* | 9/2005 | Nicolo | A61F 2/0063 606/151 |
| 2009/0187197 A1* | 7/2009 | Roeber | A61F 2/0063 606/151 |
| 2011/0011407 A1 | 1/2011 | Townsend et al. | |

* cited by examiner

PROSTHESIS FOR INGUINAL HERNIOPLASTY

The present invention relates to a prosthesis for inguinal hernioplasty and to a method for its application.

It is known that hernia is a pathological leakage of an internal organ from the cavity that normally contains it through an aperture, an anatomic channel or more generally a discontinuity in the tissues. This disease requires a surgical operation of hernioplasty during which a prosthesis for parietal reinforcement is implanted in the area affected by the hernia.

Numerous types of prostheses have been developed so far, as well as surgical methods in the aim to preserve the anatomical and functional structures of the body as much as possible, thus allowing to reduce pain and limitation in daily activities a patient may experience, as well as the incidence of relapses.

A tension free intervention method is known since 1974. This technique is based on the use of meshes having a high biocompatibility and ease of use in order to avoid anti-physiological tractions on the muscle aponeurotic structures in order to remarkably reduce the number of relapses compared to the techniques previously used. The method relies on the application of a possible prosthetic cap, better known as "plug", in the weak area of the floor of the inguinal canal, as well as of a mesh having a standardized size and shape that is placed below the fascia of the external oblique muscle. This mesh is secured without tension by way of sutures to the surrounding muscle aponeurotic structures (Lichtenstein method) or is held in place exploiting the intra-abdominal pressure only (tension free and sutureless techniques of other authors). In all these cases a fibroblastic proliferation through the mesh holes and the formation of fibrin, which begin a few hours after surgery, associated with the subsequent precipitation of collagen, biologically seal the mesh in the seat where it is arranged, thus allowing to achieve a hernioplasty without tensions.

However, interventions according to the Lichtenstein method and the like directly act on the transverse fascia only thanks to the application of plugs that are applied at specific places. However, positioning of these plugs does not reduce the risk of relapses at the plug application points, nor relapses in other positions due to the alteration of the compression forces.

Moreover, known prostheses and surgical methods do not completely address the problems of post-operative pain, which in some cases continues in the form of chronic, neuralgic or somatic pain. Moreover, known prostheses and techniques do not address serious pathological manifestations, albeit rare, due to the migration of plugs within the abdomen. In addition to this, a low risk of subsequent relapses is anyway present.

The aim of the present invention is therefore to provide a prosthesis for inguinal hernioplasty free from these drawbacks and particularly allowing to simplify hernioplasty methods while reducing post-surgery disturbs and risk of relapses. Said object is achieved with a prosthesis for inguinal hernioplasty whose main features are specified in the first claim, while other features are specified in the remaining claims.

The prosthesis for inguinal hernioplasty according to the present invention allows to strengthen, directly and without traction, the whole weak area of the floor of the inguinal canal acting on the structure comprising the transverse fascia of the inguinal hiatus. The prompt fibroblastic response stimulated by the prosthesis generates together with the transverse fascia a new wall that at the same time reinforces the side, central and medial dimples wherein a hernia occurs. The prosthesis according to the present invention thus allows a simultaneous direct reinforcement of all the weak areas of the inguinal canal, thus avoiding recurrence of hernia and relapses.

Furthermore, the particular shape of the prosthesis according to the present invention ensures its application in a mirror fashion and may thus be used for a right or left inguinal hernioplasty.

Another advantage provided by the prosthesis for inguinal hernioplasty according to the present invention is the ability to perform a simple, fast, less traumatic and painless surgical intervention leading to an earlier discharge of the patient and allowing him to quickly return to his normal daily activities.

Moreover, thanks to the small size of the prosthesis for inguinal hernioplasty according to the present invention, the risk of prosthesis corrugation after its placement in the inguinal canal is reduced, and consequently the risk of somatic pain or troublesome sensations due to the presence of a foreign body, which occur when prior art prostheses are employed.

Thanks to its special shape, the prosthesis according to the present invention remains anchored between the internal inguinal ring and the pubic tubercle.

A further advantage of the prosthesis for inguinal hernioplasty according to the present invention is that the risk of chronic neuralgic pain is avoided, these pain occurring when prior art prosthesis are used due to the interference of the prosthesis with neural structures. The risk of migration of the prosthesis in the abdomen is also avoided.

Further advantages and features of the prosthesis according to the present invention will become clear to those skilled in the art from the following detailed description and non-limiting description of an embodiment thereof with reference to the attached drawings in which.

Figure 1:
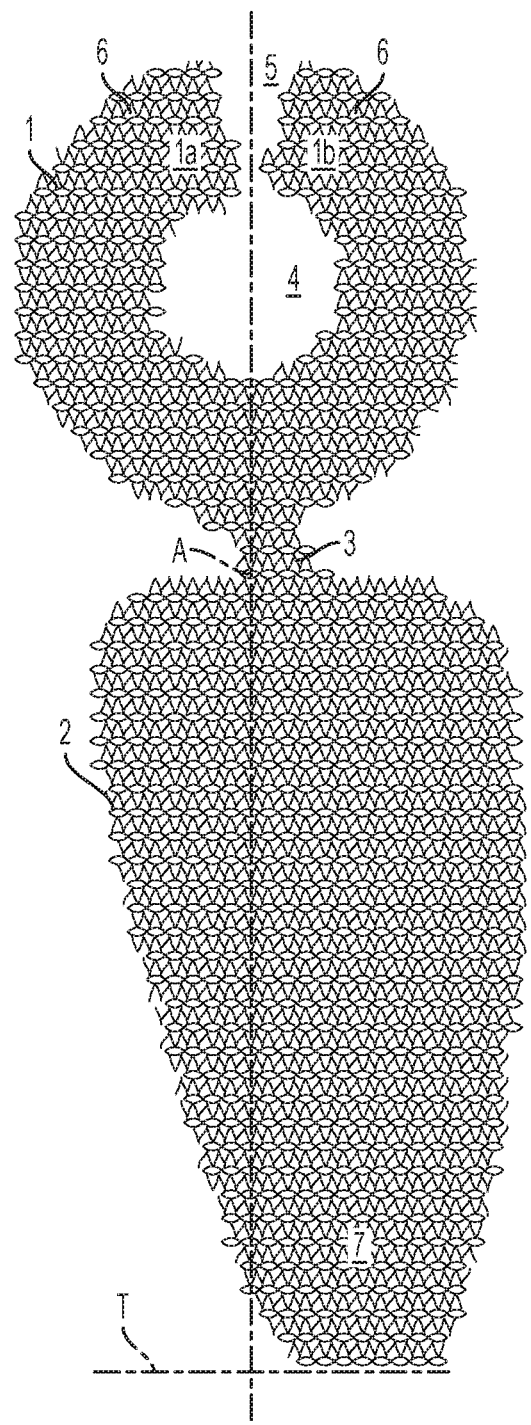
FIG. 1 shows a view of a prosthesis according to an embodiment of the present invention.

Referring to FIG. 1, it may be seen that the prosthesis for inguinal hernioplasty according to the present invention is made up of a surgical mesh and has an elongated shape extending from a first end 6 of the prosthesis to a second end 7 of the prosthesis along a longitudinal direction A. The prosthesis comprises a first portion 1 which includes said first end 6, a second portion 2 which includes said second end 7 and a third connecting portion 3 arranged between said first and second portions 1, 2. Said first portion 1 has a substantially ring or loop shape with a central hole 4. The first loop shaped portion is open or may be opened.

In the present description and in the claims, the wording "open loop shape" indicates a shape corresponding to a portion of a circular crown. The wording "open loop shape that may be opened" indicates a loop shape that may be opened by the end user with a simple cut, for example a cut with scissors performed by the surgeon during a surgical intervention.

In the present description and in the claims the wording "longitudinal direction of said second portion 2" indicates a direction along which said prosthesis is mainly extended. In FIG. 1, the longitudinal direction of the prosthesis is indicated for clarity's sake by a dashed line A.

Said first portion 1 is adapted to be arranged around the spermatic cord of the patient, possibly after the prosthetic ring has been opened by cutting. The central hole 4 of the first portion 1 is suitable to accommodate the spermatic cord. Subsequently, said first portion 1 is closed around said cord by overlapping and joining free ends 1a and 1b of the said open loop in order to form a cone that is fitted into the internal inguinal orifice. The two free ends 1a and 1b can be appropriately cut so as to reduce the diameter of the hole 4 once prosthesis shaped like a cone has been closed.

Said second end 7 of said second portion 2 is adapted to be arranged onto the pubic tubercle of the patient.

Said second portion 2 has a substantially elongated shape in said longitudinal direction A of the prosthesis, i.e. the second portion 2 has a length in said longitudinal direction A of the prosthesis that is greater than its width in a direction transverse to said longitudinal direction A.

In the present description and in the claims, the term width is to be construed as the size of the parts concerned in a transverse direction, for example perpendicular to said longitudinal direction A, and must not to be confused with the thickness of the prosthesis, which corresponds to the thickness the surgical mesh and is much lower than the other dimensions considered.

Preferably, in the prosthesis according to the present invention, said second portion 2 has a shape tapering towards said second end 7 of the prosthesis, i.e. its width at said end 7 is lower than the width at the end joined to the connecting portion 3.

In the prosthesis according to the present invention, said connecting portion 3 is a reduced portion of the prosthesis having a width, i.e. a size transverse to said longitudinal direction A, which is lower than the width of said first portion 1 as well as lower than the width of said second portion 2.

Thanks to the reduced width of the connection portion 3, the prosthesis according to the present invention integrates a prosthetic plug with a reinforcement part of the transverse fascia and may be applied and anchored between the side dimple and the pubic tubercle, avoiding the risk of migration of the plug and of corrugations of the reinforcement part either during the application step or during the permanence of the prosthesis in the inguinal canal of the patient.

The connecting portion 3 preferably has a width transverse to said longitudinal direction A which is lower than one third of the maximum width of said second portion 2 in the transverse direction.

Still more preferably the connecting portion 3 has a width transverse to said longitudinal direction A which is lower than the diameter of the central hole 4.

In particular, the connecting portion 3 preferably has a width lower than 1.0 cm, more preferably lower than 0.8 cm.

In a particularly preferred embodiment of the invention, in order to allow a better adaptation of the prosthesis to the anatomical shape of the inguinal canal, wherein the internal inguinal orifice is not arranged centrally with respect to the weak area of the transverse fascia, the shape of the prosthesis is asymmetric. In particular, considering the longitudinal direction A of the prosthesis said first portion 1 is offset relative to the second portion 2. In other words, the first portion 1 is displaced relative to the second portion 2 in a transverse direction T perpendicular to the longitudinal direction A.

In an embodiment of the invention, said first portion 1 has the shape of an open ring comprising an opening 5 connected to said central hole 4. Said opening 5 thus defines the two free ends 1a, 1b of said first portion 1.

This opening 5 is preferably arranged at a certain distance from the connecting portion 3.

In particular, given a central point of said first portion 1 corresponding to the center of the two portions of circumference delimiting the loop, the angular distance between said opening 5 and said connecting portion 3 relative to the central point is greater than 45°, preferably greater than 90°.

More preferably, said angular distance is comprised between 120° and 180°.

Even more preferably, said angular distance is about 180°, i.e. the opening 5 and said connecting portion 3 are substantially diametrically opposite to one another relative to the central point of the first portion 1.

In the present description and claims, the wording "angular distance" between said opening 5 and said connecting portion 3 with respect to the central point of the first portion, indicates the size of the angle between a first straight line connecting the central point of the first portion 1 with a point of said opening 5 and a second straight line connecting the central point with a point of said connecting portion 3.

According to a preferred embodiment of the invention, said second portion 2 has a convex shape, substantially inscribed in a trapezoid, and comprises at least one substantially straight side adjacent to said connecting portion and two curved sides. Preferably, said second portion 2 has two substantially straight sides opposite to one another and two curved sides.

The two substantially straight sides are preferably substantially parallel to each other and one of them, namely the one adjacent to the connecting portion 3, has a length greater than the length of the side that is located at the distal end 7 of the prosthesis. Furthermore, one of the two curved sides preferably has an average curvature radius greater than the other curved side.

The two substantially straight sides are preferably substantially orthogonal to said longitudinal direction of the prosthesis.

According to a preferred embodiment of the invention, said connecting portion 3 is joined to the second portion 2 approximately in the middle of the substantially straight larger side and said connecting portion 3 has substantially the shape of a parallelogram.

For simplicity of representation, in FIG. 1 the connection areas between said connecting portion 3 and said portions 1 and 2 have sharp corners, but according to an embodiment of the invention these angles may advantageously be rounded in order to provide the prosthesis with higher tensile and tear strengths.

In a particularly advantageous manner, said connecting portion 3 has substantially the shape of a rhombus, preferably having a side dimension lower than or equal to 1 cm, more preferably lower than 0.8 cm.

Preferably, said parallelogram or rhombus has two opposed internal angles whose size is comprised between 60° and 80°, more preferably between 65° and 70°. This allows to obtain the offset arrangement of the first portion 1 with respect to the second portion 2 when considering the longitudinal direction A of the prosthesis. The connecting portion 3 is joined to the second portion 2 approximately in the middle of said substantially straight larger side.

The ring forming the first portion preferably has a diameter comprised between 3.0 and 6.0 cm, more preferably such a diameter is comprised between 3.3 cm and 3.7 cm. The central hole preferably has a diameter comprised between 1.0 and 2.0 cm, more preferably comprised between 1.3 cm and 1.7 cm.

In the second portion 2 one of the substantially straight sides has a length comprised between 2.0 cm and 3.5 cm, more preferably comprised between 2.0 cm and 3.1 cm. The other substantially straight side instead has a length comprised between 0.5 and 1.5 cm, more preferably comprised between 0.7 cm and 1.3 cm.

The greater width of the second portion 2 in a direction transverse to said longitudinal direction A, i.e. in a direction parallel to said substantially straight larger side, is preferably greater than the size of the substantially straight larger side. Preferably, said greater width of the second portion 2 is comprised between 2.0 cm and 4.0 cm, more preferably comprised between 2.3 cm and 3.3 cm.

This greater width of the second portion 2 is preferably positioned in the part of the portion 2 that is closer to said first portion 1, more preferably within the upper half of the second portion 2 with respect to the longitudinal direction.

The distance between said substantially straight side having a greater length and the other substantially straight side, i.e. the length of the second portion 2 in the longitudinal direction A, is comprised between about 3.0 cm and 6.0 cm, more preferably comprised between 5.2 cm and 5.8 cm.

According to a particularly preferred embodiment, said connecting portion 3 substantially has the shape of a rhombus having a side of about 0.5 cm. The first ring shaped portion has a diameter of about 3.5 cm, while said central hole has a diameter of about 1.5 cm. The substantially straight sides have lengths equal to 2.8 cm and 1.0 cm respectively and the distance between said substantially straight side having a greater length and the other substantially straight side is about 5.5 cm. The greater width of the second portion 2 is about 3 cm.

The surgical prosthesis according to the present invention is formed by a mesh made of any material suitable for the manufacturing of prostheses for the abdominal wall.

The prosthesis according to the present invention is preferably made of polypropylene.

The prosthesis according to the present invention may be applied by way of a new surgical method of simple implementation, which is less traumatic and painless compared to prior art methods. This method also allows early discharge of patients, who may quickly return to their normal daily activities, and is free from outcomes after surgery. Thanks to the arrangement of the prosthesis at a more specific target area, the risk of corrugations and interference with nerve structures is reduced.

The surgical method for the application of the prosthesis according to the present invention comprises in a known way a step of cutting the superficial layers and of opening of the aponeurosis of the external oblique muscle.

Subsequently, localization of the spermatic cord is carried out. According to the method of the invention, there is no need to identify and isolate the neural structures under the aponeurosis of the external oblique muscle, i.e. the iliohypogastric nerve and the ilioinguinal nerve. A medial longitudinal cutting of the cremaster muscle and the of external spermatic fascia (fibrous cremaster sheath) is then performed a with diathermic coagulation device; these parts are then separated from the elements of the spermatic cord up to the inguinal ligament.

It is known that the cremaster muscle, which is the continuation of the internal abdominal oblique muscle, also is continuous to the pubic tubercle and the inguinal ligament and that it reaches the spermatic cord where it is arranged between the external and internal spermatic fasciae, eversion of the transverse fascia, also called common vaginal tunic.

Figure 2:
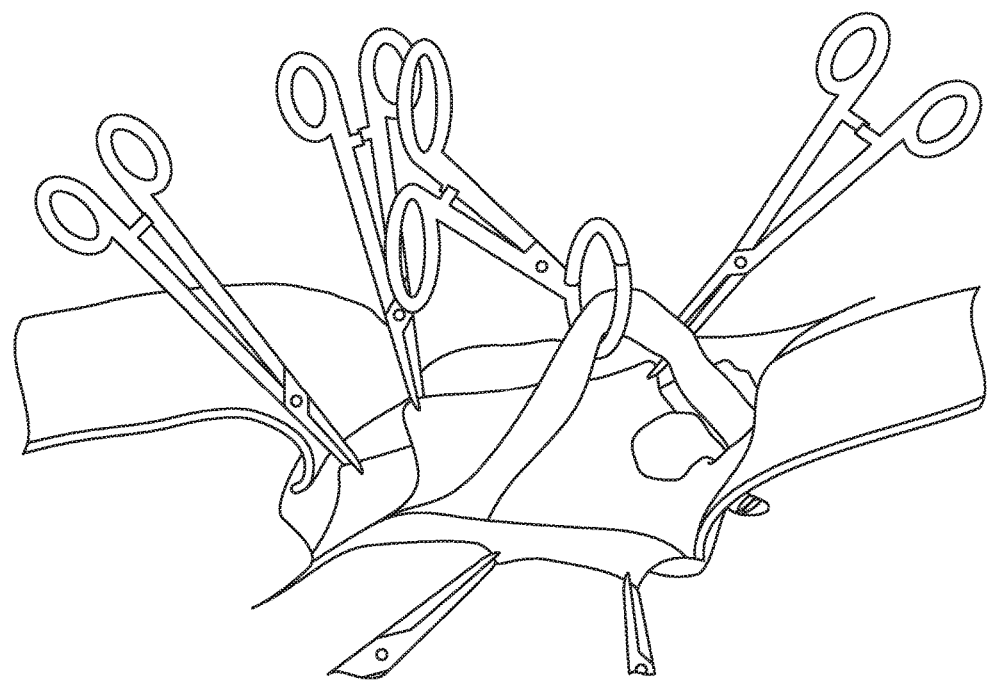
FIG. 2 shows a first step of the application of the prosthesis of FIG. 1 into the inguinal canal.

After localization of the medial edges of the fibrous cremaster sheath e.g. by way of Klemmer forceps as shown in FIG. 2, the hernial sac is identified and the elements of the spermatic cord are separated.

In the case of a direct or internal oblique hernia the hernial sac must be isolated from the surrounding structures, as well as from the transverse fascia up to the hernial neck, if any.

The weak area is then flattened by way of plication of the transverse fascia. The internal inguinal ring intended to receive the first portion 1 of the prosthesis is then prepared.

In the case of an external oblique hernia it is necessary to separate the hernial sac up to the internal inguinal ring so as to allow its complete reduction in the abdomen. The possible presence of a prehernial lipoma may be treated by its resection, when cumbersome, and by its reduction in the abdomen together with the hernial sac.

In all cases, a prosthesis according to the present invention is applied to the rear wall as a reinforcement.

If the opening 5 is not already present, the first portion 1 is cut and arranged so as to surround the elements of the spermatic cord by forming a prosthetic cone around them; such a cone is obtained by approaching the ends 1a and 1b of the first portion 1. These ends are appropriately cut, approached and arranged atop of each other in order to adapt the size of the prosthetic cone to the diameter of the spermatic cord. Once reached the correct size the prosthetic cone is closed around the spermatic cord by way of a suture point.

Figure 3:
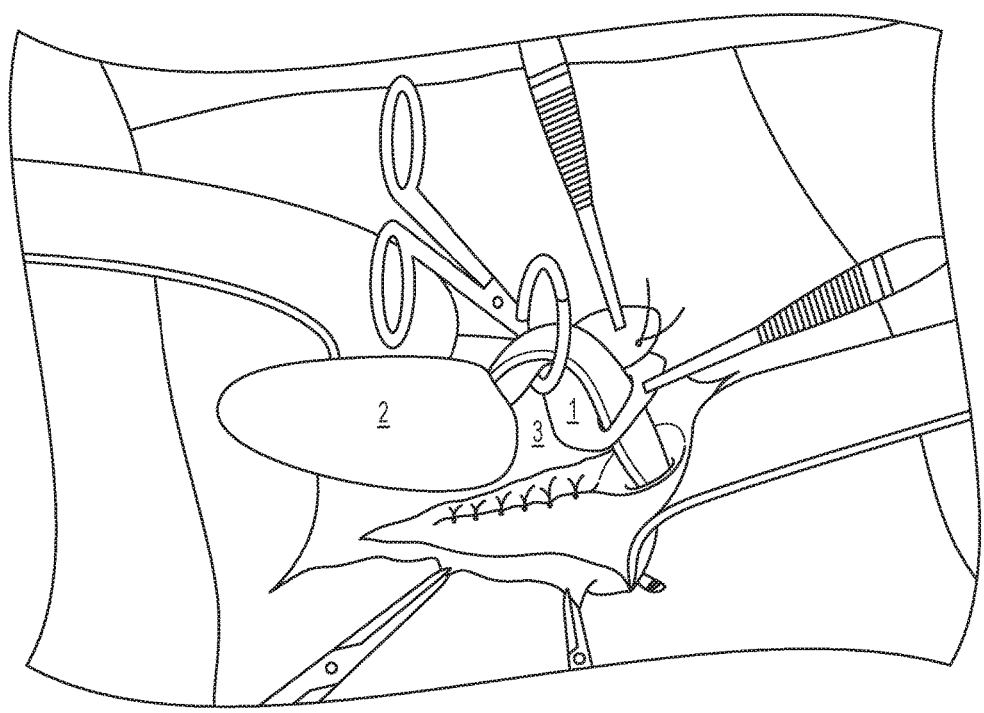
FIG. 3 shows a second step of the application of the prosthesis of FIG. 1 in the inguinal canal.

As shown in FIG. 3, the prosthetic cone is then fitted into the internal inguinal orifice, while the elements of the spermatic cord are preferably moved upwards, e.g. by way of a Bottini forceps, in order to facilitate this maneuver. The prosthetic cone so fitted helps to repair the weak area located at the internal inguinal ring, i.e. the side dimple. The particular shape of the prosthesis according to the present invention obtained starting from its first portion allows to avoid to interfere and press the underlying vascular structures.

In the of case of cumbersome hernias with a large internal inguinal ring, a prosthesis with a first portion 1 having a larger diameter may be used, i.e. a diameter closer to the upper end of the range 3.0 to 6.0 cm. A plastic surgery of the ring by way of detached suture points may possibly be carried out.

The connecting portion 3 comes out from the internal inguinal ring and the prosthesis according to the present invention extends along the second portion 2, which is placed over the transverse fascia. Since the first portion 1 and the second portion 2 are not completely aligned along said longitudinal direction A, it is possible to fully stretch the second portion 2 on the floor of the inguinal canal in order to reinforce the central and medial dimples. The end of the second portion 2 is secured by way of an absorbable suture point at the level of the pubis bypassing the periosteum.

It will be understood that the prosthesis according to the present invention may be applied in a mirror fashion, thus ensuring the possibility of carrying out a right or left hernioplasty by using the same prosthesis.

The prosthesis so applied, lies with the side of the second portion having the larger average radius of curvature (i.e. the left one shown in FIG. 1) arranged at the concavity of the inguinal ligament and reaches the associated tendon medially, or above it (depending on the size of the patient) so as not to cause wrinkles. The complete stretching of the prosthesis prevents the formation of gaps that would delay the infiltration of fibroblasts, thus favoring the seizure of the prosthesis, infection and relapses.

At this point, it is possible to proceed to the plastic surgery of the internal inguinal ring with detached absorbable suture points.

Figure 4:
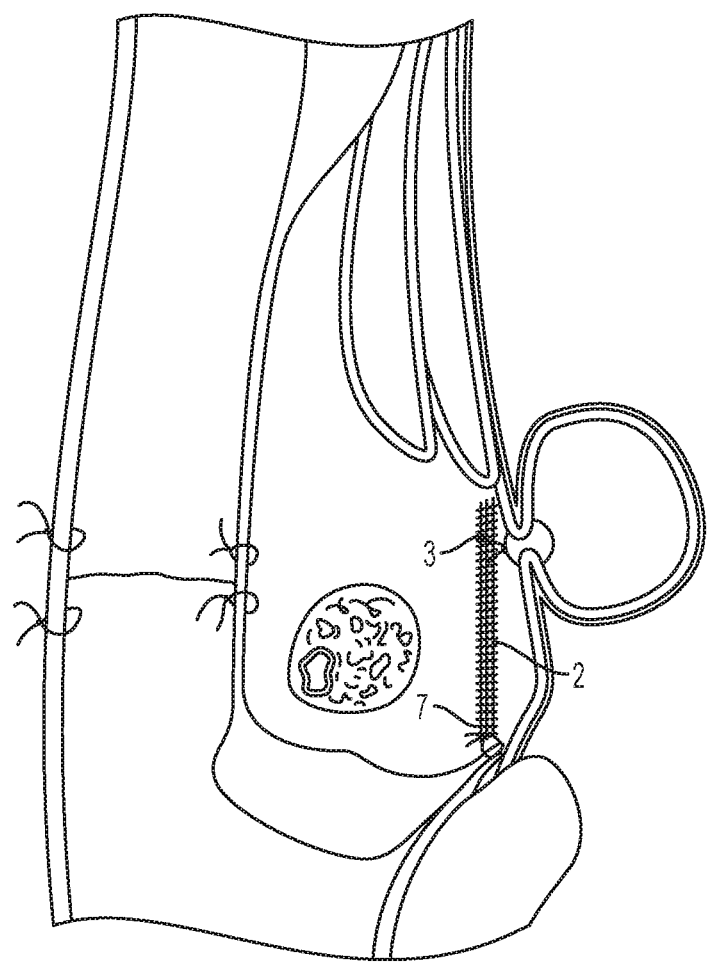
FIG. 4 shows a sectional view of the inguinal canal wherein the prosthesis of FIG. 1 is applied.

FIG. 4 shows a sectional view of the inguinal canal wherein the prosthesis according to the present invention is applied. It may be seen that the second end 7 of the second portion 2 overlaps the pubic tubercle, generally by about 1 cm, and is fixed at this point e.g. with an absorbable suture point bypassing the periosteum.

Finally, the recovery of the medial edge of the cremaster muscle, which had previously been displaced, is carried out. This muscle is arranged to cover the prosthesis according to the present invention by suturing it to the aponeurotic muscle structures, for example, by continuous suturing with absorbable suture points. The cremaster play a covering role only, which prevents adhesion of the cord below the prosthesis. A possible injury during cutting operations may simply be sutured with absorbable suture points. After having arranged the cord back to its seat, the surgical intervention is completed by closing the external oblique muscle fascia and the superficial layers up to the pubic tubercle with absorbable suture points.

The prosthesis according to the present invention anchored between the internal inguinal orifice and the pubic tubercle in order to reinforce the rear wall is arranged between cremaster and transverse fascia and well stretched therebetween. The cord under the aponeurosis and the pressure exerted by the tissues contribute to press the prosthesis. A prompt fibroblastic response fixes the mesh thus forming a good triple retaining layer and preventing formation of gaps that might cause secondary hematoma and/or seroma, as well as entrapment of nerve structures, which would cause chronic pain difficult to treat.

In women, after applying the mesh as described before with reference to men, the prosthesis may be left anchored and not covered. It is clear that in this case the element that passes through the central hole 4 of the first portion 1 is the round ligament that can safely remain in contact with the mesh. A thin round ligament may also be cut and reduced into the abdomen. In these cases the central hole 4 must be closed by application of a suture point made of a non-absorbable material.

According to an embodiment of the invention, the surgical method is carried out under local anesthesia.

The invention claimed is:

1. A prosthesis for inguinal hernioplasty made up of a surgical mesh extending from a first end (6) to a second end (7) along a longitudinal direction (A) and comprising a first portion (1) that includes said first end (6), a second portion (2) that includes said second end (7) and a connecting portion (3) arranged between said first portion (1) and said second portion (2), wherein said first portion (1) has a substantially loop shape that is open or may be opened and is provided with a central hole (4), wherein said second portion (2) has a substantially elongated shape in said longitudinal direction (A), wherein said connecting portion (3) has a width transverse to said longitudinal direction (A) smaller than the widths of said first portion (1) and said second portion (2) transverse to said longitudinal direction (A), and wherein said first portion (1) is offset relative to said second portion (2) transversely relative to said longitudinal direction (A).

2. The prosthesis according to claim 1, characterized in that said connecting portion (3) has a width transverse to said longitudinal direction (A) that is lower than one third of the maximum width of said second portion (2) in a direction transverse to said longitudinal direction (A).

3. The prosthesis according to claim 1, characterized in that said second portion (2) has a shape tapering towards said second end (7) of the prosthesis.

4. The prosthesis according to claim 1, characterized in that said first portion (1) has the shape of an open ring and has an opening (5) which is connected to said central hole (4) and which defines two free ends (1a, 1b) of said first portion (1).

5. The prosthesis according to claim 4, characterized in that an angular distance between said opening (5) and said connecting portion (3) with respect to a central point to the first portion (1) is greater than 45°.

6. The prosthesis according to claim 5, characterized in that the angular distance is comprised between 120° and 180°.

7. The prosthesis according to claim 1, characterized in that said second portion (2) has a convex shape and has two opposite sides that are substantially straight and two curved sides, wherein one of said two substantially straight sides has a length greater than the other one and is adjacent to said connecting portion (3).

8. The prosthesis according to claim 1, characterized in that said connecting portion (3) has substantially the shape of a parallelogram.

9. The prosthesis according to claim 8, characterized in that said connecting portion (3) has substantially the shape of a rhombus having a side the dimension of which is lower than or equal to 1.0 cm.

10. The prosthesis according to claim 8, characterized in that said parallelogram has two internal angles of size between 60° and 80°.

11. The prosthesis according to claim 1, characterized in that the loop formed by said first portion (1) has a diameter comprised between 3.0 and 6.0 cm, and that said central hole has a diameter comprised between 1.0 and 2.0 cm.

12. The prosthesis according to claim 1, characterized in that in said second portion (2), a substantially straight side has a greater length between 2.0 cm and 3.5 cm, and another substantially straight side has a length comprised between 0.5 and 1.5 cm.

13. The prosthesis according to claim 12, characterized in that the distance between said substantially straight side having the greater length and the another substantially straight side is comprised between about 3.0 cm and 6.0 cm.

14. The prosthesis according to claim 1, characterized in that a maximum width of said second portion (2) in a direction transverse to said longitudinal direction (A) is comprised between 2.0 cm and 4.0 cm.

* * * * *